US008840938B2

(12) United States Patent
Warnock

(10) Patent No.: US 8,840,938 B2
(45) Date of Patent: Sep. 23, 2014

(54) BIOAVAILABILITY ENHANCING COMPOSITION

(76) Inventor: W. Matthew Warnock, Sandy, UT (US)

( * ) Notice: Subject to any disclaimer, the term of this patent is extended or adjusted under 35 U.S.C. 154(b) by 0 days.

(21) Appl. No.: 13/446,786

(22) Filed: Apr. 13, 2012

(65) Prior Publication Data

US 2012/0263808 A1 Oct. 18, 2012

Related U.S. Application Data

(60) Provisional application No. 61/475,102, filed on Apr. 13, 2011.

(51) Int. Cl.
| | |
|---|---|
| *A61K 36/67* | (2006.01) |
| *A61K 36/906* | (2006.01) |
| *A61K 36/81* | (2006.01) |
| *A61K 36/00* | (2006.01) |
| *A61K 36/54* | (2006.01) |
| *A61K 31/16* | (2006.01) |
| *A61K 31/445* | (2006.01) |
| *A61K 31/12* | (2006.01) |
| *A23L 1/30* | (2006.01) |
| *A61K 31/4525* | (2006.01) |
| *A61K 31/165* | (2006.01) |
| *A61K 36/758* | (2006.01) |
| *A61K 31/164* | (2006.01) |
| *A61K 36/9068* | (2006.01) |
| *A61K 36/61* | (2006.01) |

(52) U.S. Cl.
CPC .............. *A61K 31/12* (2013.01); *A23L 1/3002* (2013.01); *A61K 31/4525* (2013.01); *A61K 31/165* (2013.01); *A61K 36/67* (2013.01); *A61K 36/54* (2013.01); *A61K 36/758* (2013.01); *A61K 31/164* (2013.01); *A61K 36/9068* (2013.01); *A61K 31/16* (2013.01); *A61K 36/61* (2013.01); *A61K 36/81* (2013.01)
USPC ........... 424/734; 424/756; 424/760; 424/725; 424/739; 514/627; 514/321; 514/678

(58) Field of Classification Search
None
See application file for complete search history.

(56) References Cited

U.S. PATENT DOCUMENTS 5,744,161 A * 4/1998 Majeed et al. ................ 424/464
5,972,382 A 10/1999 Majeed et al.

OTHER PUBLICATIONS

Yamazaki et al. Food Chemistry (2007) 171-177.*
Website document entitled "Cinnamon Medicinal Properties". (available at http://www.botanical-online.com/english/cinnamon.htm). Downloaded from website Oct. 1, 2013.*
Website document entitled "Cloves nutrition Facts". (Available at http://www.nutrition-and-you.com/cloves.htm). Downloaded from website Oct. 1, 2013.*
Hisatomi et al. J. Agric. Food Chem. (2000) 48, 4924-3928.*
Lee et al. Food Chemistry (2001) 443-448.*
Bouraoui A, Toumi A, Mustapha HB, et al. "Effects of capsicum fruit on theophylline absorption and bioavailability in rabbits." Drug Nutrient Interactions, Jan. 1988.
L. Srinivasan, Black pepper and its pungent principle-piperine: a review of diverse physiological effects, Critical Reviews of Food Science and Nutrition, Jan. 2007.
K. Platel et al., "Influence of dietary spices and their active principles on pancreatic digestive enzymes in albino rats," Die Nahrung, Jan. 2000.
Singletary, K., "Black Pepper: Overview of Health Benefits," Nutrition Today, Jan./Feb. 2010.
Wu, K., et al. "Effects of Ginger on Gastric Emptying and Motility in Healthy Humans," European Journal of Gastroenterology and Hepatology, May 2008.

* cited by examiner

*Primary Examiner* — Chris R Tate
*Assistant Examiner* — Russell Fiebig
(74) *Attorney, Agent, or Firm* — Kunzler Law Group

(57) ABSTRACT

For enhancing bioavailability, a composition is administered comprising a Transient Receptor Potential cation channel subfamily V member 1 (TRPV1) agonist with a combined Scoville Heat Unit (SHU) milligram (mg) dose in the range of 280,000 to 400,000 SHU mg.

7 Claims, 3 Drawing Sheets

α-Sanshool

γ-Sanshool

β-Sanshool

δ-Sanshool

Hydroxy α-Sanshool

Hydroxy β-Sanshool 6-shogaol 6-gingerol

Piperine

Capsaicin

BIOAVAILABILITY ENHANCING COMPOSITION

CROSS-REFERENCE TO RELATED APPLICATIONS

This application claims priority to U.S. Provisional Patent Application No. 61/475,102 entitled "BIOAVAILABILITY ENHANCING COMPOUND" and filed on Apr. 13, 2011 for W. Matthew Warnock, which is incorporated herein by reference.

BACKGROUND

1. Field

The subject matter disclosed herein relates to bioavailability and more particularly relates to bioavailability enhancement.

2. Description of the Related Art

Nutrients must be digested in order to benefit the body. However, some nutrients are difficult to digest.

BRIEF DESCRIPTION OF THE DRAWINGS

A more particular description of the embodiments of the invention will be rendered by reference to specific embodiments that are illustrated in the appended drawings. Understanding that these drawings depict only some embodiments and are not therefore to be considered to be limiting of scope, the embodiments will be described and explained with additional specificity and detail through the use of the accompanying drawings, in which.

DETAILED DESCRIPTION

Figure 1A:
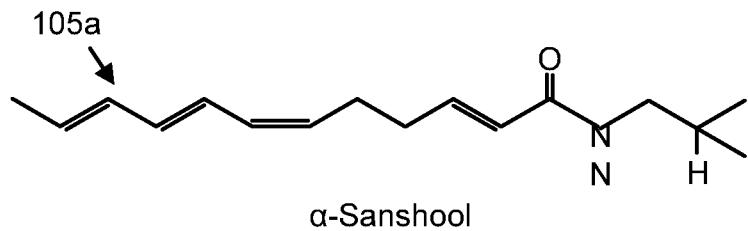
FIGS. 1A-F are molecular structure drawings of sanshool.
Figure 1B:
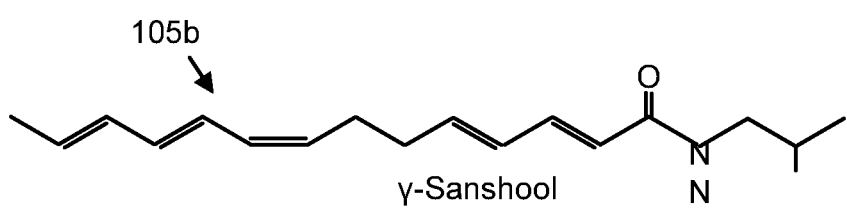
Figure 1C:
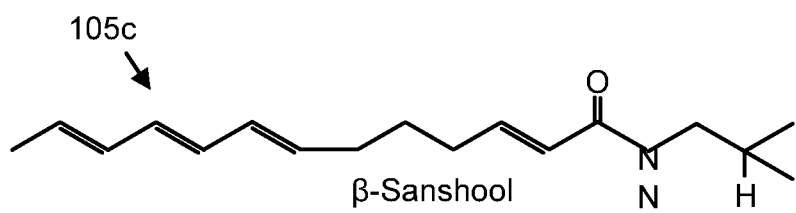
Figure 1D:
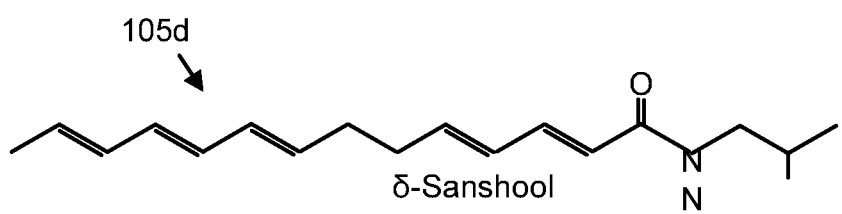
Figure 1E:
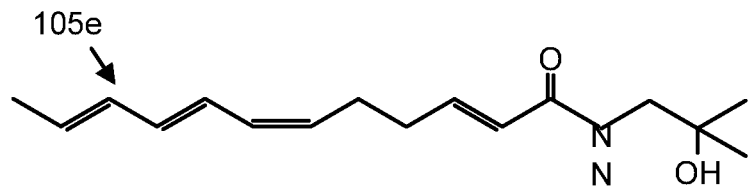
Figure 1F:
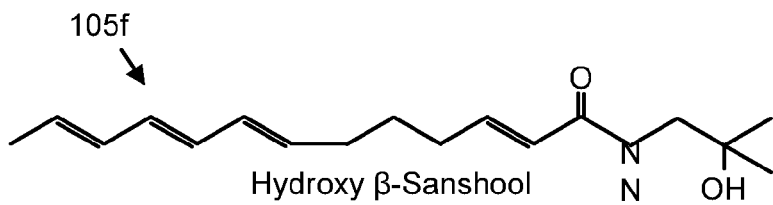

Reference throughout this specification to "one embodiment," "an embodiment," or similar language means that a particular feature, structure, or characteristic described in connection with the embodiment is included in at least one embodiment. Thus, appearances of the phrases "in one embodiment," "in an embodiment," and similar language throughout this specification may, but do not necessarily, all refer to the same embodiment, but mean "one or more but not all embodiments" unless expressly specified otherwise. The terms "including," "comprising," "having," and variations thereof mean "including but not limited to," unless expressly specified otherwise. An enumerated listing of items does not imply that any or all of the items are mutually exclusive, unless expressly specified otherwise. The terms "a," "an," and "the" also refer to "one or more" unless expressly specified otherwise.

Nutrients must be digested in order to be of use to the body. Digestion is stimulated by the activation of Transient Receptor Potential cation channel subfamily V member 1 (TRPV1) receptors in the digestive tract. The TRPV1 receptors are activated by both by heat greater than 43° Celsius and TRPV1 agonists including vanilloids such as capsaicin, vanillin, vanillic acid, and vanillyl mandelic acid, piperine, gingerol or 6-gingerol, shogaol or 6-shogaol, sanshools including α-sanshool, β-sanshool, γ-sanshool, δ-sanshool, hydroxyl α-sanshool, and hydroxyl β-sanshool, and allyl isothiocyanate. When TRPV1 receptors are activated by TRPV1 agonists, blood flow to the area of the TRPV1 receptor is increased, increasing capillary action in the walls of the gastrointestinal tract, and resulting in increased digestion and absorption of nutrients.

TRPV1 agonists such as capsaicin and/or piperine have been shown to increase the absorption and bioavailability of compounds such as theophylline. In addition, Ginger has been shown to improve digestion. The following are examples of increased bioavailability from capsaicin, piperine, and ginger.

Example 1

Ten male rabbits were given an oral administration of theophylline (20 mg/kg) with and without a ground capsicum fruit suspension in a sustained release capsule. The absorption and bioavailability of theophylline was then measured. Concomitant absorption of capsicum increased levels of theophylline from 86.06+/−9.78 mg H/liter to 138.32+/−17.27 mg H/liter, with a P of less than 0.001. Peak theophylline plasma levels increased from 6.65+/−0.76 to 8.78+/−0.98 mg/liter, with a P of less than 0.01, and mean residence times of theophylline increased from 14.94+/−2.97 to 20.98+/−5.75 H, with a P of less than 0.001. The rabbits were given a second administration the capsicum suspension 11 hours later, producing a new rise of theophylline plasma levels in every rabbit. See Bouraoui A, Toumi A, Mustapha H B, et al. "Effects of capsicum fruit on theophylline absorption and bioavailability in rabbits," Drug Nutrient Interactions, 1998.

Example 2

Black pepper, which contains piperine, was found to significantly increase the absorption of nutrients, plant chemicals, and medications when taken internally. Black pepper increased the absorption through the intestinal tract, possibly by altering the permeability of the intestinal wall, slowing down gut motility, and stimulating intestinal enzymes. Srinivasan, L. "Black pepper and its pungent principle-piperine: a review of diverse physiological effects," Critical Reviews of Food Science and Nutrition, 2007.

Example 3

Rats given piperine showed an improved secretion of amylase, lipase and trypsin from the pancreas. Increasing the production of these digestive enzymes may support the digestion and breakdown of fats, carbohydrates and proteins in the body. Platel, K. et al., "Influence of dietary spices and their active principles on pancreatic digestive enzymes in albino rats," Die Nahrung, January, 2000.

Example 4

The intake of black pepper extract, which contains piperine, stimulated stomach secretions and affected the rapidity of movement of food through the digestive tract in mice and rats. The addition of piperine to a dose of curcumin greatly increased the serum concentration of curcumin by up to 2000%. Singletary, K., "Black Pepper: Overview of Health Benefits," Nutrition Today, 2010 January/February.

Example 5

Men who didn't eat or drink for eight hours but then had 1,200 mg of ginger before eating a bowl of soup were more likely to experience stomach muscle contractions that emptied the stomach contents into the small intestine than subjects taking a placebo. Subjects taking the placebo also had more digestive discomfort. Wu, K., et al. "Effects of Ginger on Gastric Emptying and Motility in Healthy Humans," European Journal of Gastroenterology and Hepatology, May 2008.

Unfortunately, TRPV1 agonists such as capsaicin may also cause a number of undesirable side effects when administered to a subject. The side effects may include increased risk of bleeding, reduced oral drug bioavailability, reduced intestinal absorption of glucose.

Embodiments disclosed herein increase the absorption and bioavailability of nutrients while mitigating the side effects of ingesting TRPV1 agonists such as capsaicin by combining herbs with TRPV1 agonists. The combination provides TRPV1 agonists with a combined Scoville Heat Unit (SHU) milligram (mg) dose in the range of 280,000 to 400,000 SHU mg. SHU as used herein as a measure of TRPV1 activation. SHU mg is calculated as the SHU of a TRPV1 agonist multiplied by the milligrams of the TRPV1 agonist in a compound.

By employing multiple TRPV1 agonists with dissimilar side effects in a composition, a therapeutic dose of TRPV1 agonists is supplied while minimizing the side effects. In one embodiment, the TRPV1 agonists include at least one of capsaicin, piperine, 6-gingerol, 6-shogaol, α-sanshool, β-sanshool, γ-sanshool, δ-sanshool, hydroxyl α-sanshool, and hydroxyl β-sanshool.

FIG. 1A-F are molecular structure drawings of Sanshool 105. Embodiments include α-sanshool 105a in FIG. 1A, γ-sanshool 105b in FIG. 1B, β-sanshool 105c in FIG. 1C, δ-sanshool 105d in FIG. 1D, hydroxyl α-sanshool 105e in FIG. 1E, hydroxyl β-sanshool 105f in FIG. 1F.

Figure 2:
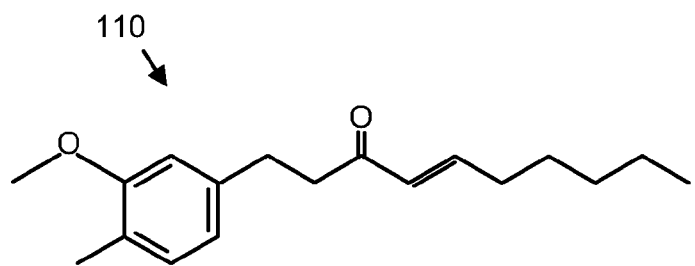
FIG. 2 is a molecular structure drawing of 6-shogaol.
Figure 3:
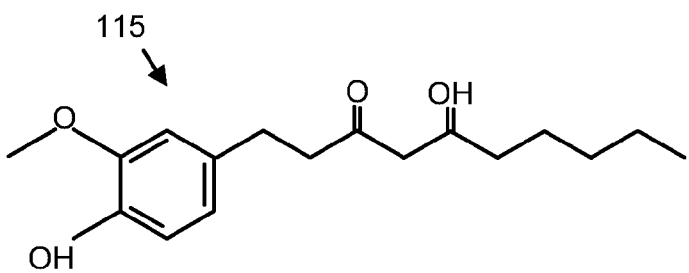
FIG. 3 is a molecular structure drawing of 6-gingerol.
Figure 4:
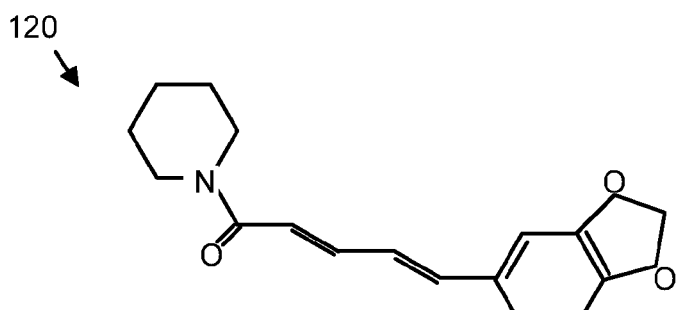
FIG. 4 is a molecular structure drawing of piperine.
Figure 5:
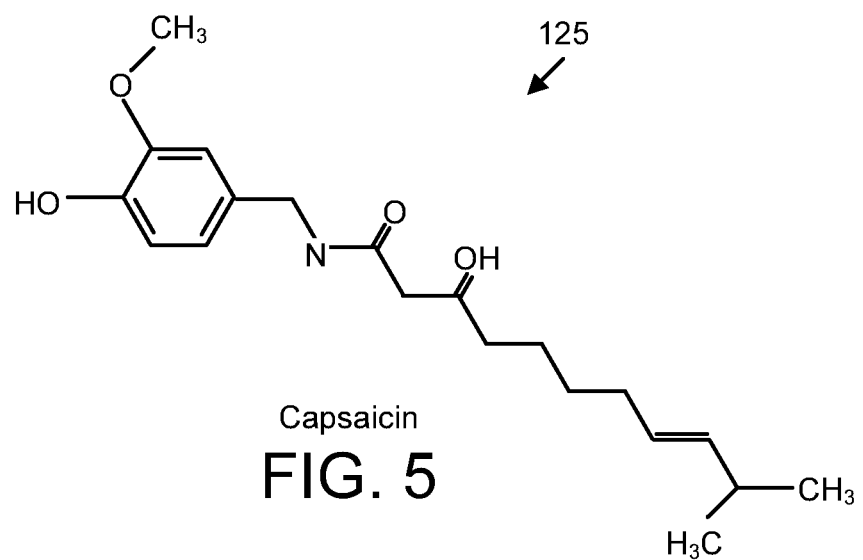
FIG. 5 is a molecular structure drawing of capsaicin.

FIG. 2 is a molecular structure drawing of 6-shogaol. FIG. 3 is a molecular structure drawing of 6-gingerol. FIG. 4 is a molecular structure drawing of piperine. FIG. 5 is a molecular structure drawing of capsaicin.

In one embodiment, the TRPV1 agonist is supplied by herbs from at least one of a Zingiber family herb, a Capsicum family herb, a Piper family herb, and a Zanthoxylum family herb. The Capsicum family herb may be selected from the group consisting of *Capsicum annuum, Capsicum chinense*, and *Capsicum frutescens*. The Piper family herb may be selected from the group consisting of *Piper nigrum* and *Piper longum*.

In one embodiment, the TRPV1 agonist is supplied by *Zingiber officinale, Piper nigrum, Capsicum annuum*, and *Zanthoxylum piperitum*. The *Zingiber officinale* may supply TRPV1 agonist in the range of 170,000 to 250,000 SHU mg. The *Piper nigrum* may supply TRPV1 agonist in the range of 20,000 to 30,000 SHU mg. The *Capsicum annuum* may supply TRPV1 agonist in the range of 60,000 to 100,000 SHU mg. In addition, the *Zanthoxylum piperitum* may supply TRPV1 agonist in the range of 20,000 to 30,000 SHU mg.

In an alternate embodiment, the TRPV1 agonist is supplied by *Zingiber officinale, Piper nigrum*, and *Capsicum annuum*. The *Zingiber officinale* may supply TRPV1 agonist in the range of 190,000 to 265,000 SHU mg. The *Piper nigrum* may supply TRPV1 agonist in the range of 25,000 to 35,000 SHU mg. The *Capsicum annuum* may supply TRPV1 agonist in the range of 65,000 to 100,000 SHU mg.

Table 1 shows herbs, the active TRPV1 agonist in each herb, the SHU for each pure TRPV1 agonist per mg, the percentage of the TRPV1 agonist in herb, and the adjusted SHU supplied by a milligram of TRPV1 agonist.

TABLE 1

| Herb | TRPV1 Agonist | SHU of pure Agonist | Percent Agonist | Adjusted SHU |
|---|---|---|---|---|
| Zingiber officinale | 6-gingerol | 60,000 | 6.00% | 3,600 |
| | 6-shogaol | 160,000 | 6.00% | 9,600 |
| | Total | | | 13,200 |
| Piper nigrum | piperine | 100,000 | 7.15% | 7,150 |
| Capsicum annuum | capsaicin | 16,000,000 | 0.25% | 40,000 |
| Xanthoxylum piperitum | α-sanshool | 80,000 | 0.46% | 368 |
| | β-sanshool | 70,000 | 0.07% | 49 |
| | γ-sanshool | 110,000 | 0.19% | 209 |
| | δ-sanshool | 110,000 | 0.02% | 22 |
| | α-hydroxy-sanshool | 26,000 | 2.38% | 619 |
| | β-hydroxy-sanshool | 13,000 | 0.27% | 35 |
| | | | | 1302 |

The following formulations in Table 2 show combinations of *Zingiber officinale, Piper nigrum, Capsicum annuum*, and *Zanthoxylum piperitum* that may provide the TRPV1 agonists in the composition. The formulations are only illustrative of embodiments of compositions, and are not limiting.

TABLE 2

| | SHU mg |
|---|---|
| Formulation 1 | |
| Zingiber officinale | 170,000 |
| Piper nigrum | 20,000 |
| Capsicum annuum | 60,000 |
| Xanthoxylum piperitum | 30,000 |
| Total SHU mg | 280,000 |
| Formulation 2 | |
| Zingiber officinale | 250,000 |
| Piper nigrum | 30,000 |
| Capsicum annuum | 100,000 |
| Xanthoxylum piperitum | 20,000 |
| Total SHU mg | 400,000 |
| Formulation 3 | |
| Zingiber officinale | 200,000 |
| Piper nigrum | 25,000 |
| Capsicum annuum | 80,000 |
| Xanthoxylum piperitum | 25,000 |
| Total SHU mg | 330,000 |
| Formulation 4 | |
| Zingiber officinale | 180,000 |
| Piper nigrum | 22,000 |
| Capsicum annuum | 68,000 |
| Xanthoxylum piperitum | 20,000 |
| Total SHU mg | 290,000 |
| Formulation 5 | |
| Zingiber officinale | 230,000 |
| Piper nigrum | 28,000 |
| Capsicum annuum | 92,000 |
| Xanthoxylum piperitum | 30,000 |
| Total SHU mg | 380,000 |
| Formulation 6 | |
| Zingiber officinale | 230,000 |
| Piper nigrum | 28,000 |

TABLE 2-continued

| | SHU mg |
|---|---|
| Capsicum annuum | 92,000 |
| Xanthoxylum piperitum | 30,000 |
| Total SHU mg Formulation 7 | 380,000 |
| Zingiber officinale | 170,000 |
| Piper nigrum | 30,000 |
| Capsicum annuum | 100,000 |
| Xanthoxylum piperitum | 30,000 |
| Total SHU mg Formulation 8 | 330,000 |
| Zingiber officinale | 170,000 |
| Piper nigrum | 30,000 |
| Capsicum annuum | 60,000 |
| Xanthoxylum piperitum | 30,000 |
| Total SHU mg Formulation 9 | 290,000 |
| Zingiber officinale | 190,000 |
| Piper nigrum | 25,000 |
| Capsicum annuum | 65,000 |
| Xanthoxylum piperitum | 30,000 |
| Total SHU mg Formulation 10 | 310,000 |
| Zingiber officinale | 245,000 |
| Piper nigrum | 35,000 |
| Capsicum annuum | 100,000 |
| Xanthoxylum piperitum | 20,000 |
| Total SHU mg | 400,000 |

The composition of *Zingiber officinale, Piper nigrum, Capsicum annuum*, and *Zanthoxylum piperitum* may be a simple blend. Alternatively the composition may be an extract of a blend of the *Zingiber officinale, Piper nigrum, Capsicum annuum*, and *Zanthoxylum piperitum*. In one embodiment, a separate extract of each of the *Zingiber officinale, Piper nigrum, Capsicum annuum*, and *Zanthoxylum piperitum* is prepared and combined to form the composition.

The composition may further comprise *Cinnamomum verum* and *Syzygium aromaticum*. In one embodiment, the *Zingiber officinale* by weight is in the range of 20 to 30%, the *Piper nigrum* by weight in the range of 2 to 6%, the *Capsicum annuum* by weight is in the range of 2 to 4%, and the *Zanthoxylum piperitum* by weight is in the range of 25 to 35%. In a certain embodiment the composition comprises the *Zingiber officinale* by weight in the range of 24 to 26%, the *Piper nigrum* by weight in the range of 3 to 5%, the *Capsicum annuum* by weight in the range of 2.5 to 3.5%, and the *Zanthoxylum piperitum* by weight in the range of 27 to 29%.

The formulations in Table 3 show combinations of *Zingiber officinale, Piper nigrum, Capsicum annuum, Zanthoxylum piperitum, Cinnamomum verum*, and *Syzygium aromaticum* by weight that may provide the TRPV1 agonists. The formulations are only illustrative of compositions, and are not limiting.

TABLE 3

| | Percentage Weight |
|---|---|
| Formulation 11 | |
| Zingiber officinale | 25% |
| Piper nigrum | 4% |
| Capsicum annuum | 3% |

TABLE 3-continued

| | Percentage Weight |
|---|---|
| Xanthoxylum piperitum | 28% |
| Cinnamomum verum | 24% |
| Syzygium aromaticum | 6% |
| Formulation 12 | |
| Zingiber officinale | 20% |
| Piper nigrum | 3% |
| Capsicum annuum | 3% |
| Xanthoxylum piperitum | 29% |
| Cinnamomum verum | 32% |
| Syzygium aromaticum | 13% |

In one embodiment, formulations are combined with at least 20% of total weight of at least one of bioavailable silicon, a chelate, bamboo, and/or *Equisetum arvense* (horsetail). The TRPV1 agonists may increase the bioavailability of silicon in the bioavailable silicon, chelate, bamboo, and/or *Equisetum arvense*.

Embodiments may be practiced in other specific forms. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A bioavailability enhancing composition comprising an effective amount of a Transient Receptor Potential cation channel subfamily V member 1 (TRPV1) agonist, wherein the TRPV1 agonist comprises *Zingiber officinale, Piper nigrum*, and *Zanthoxylum piperitum* with a combined Scoville Heat Unit (SHU) milligram (mg) dose in the range of 280,000 to 400,000 SHU mg, wherein SHU mg dose is calculated as the SHU of the TRPV1 agonist multiplied by milligrams of the TRPV1 agonist, wherein the *Zingiber officinale* is in the range of 20 to 30% by weight of the composition, the *Piper nigrum* is in the range of 2 to 6% by weight of the composition, and the *Zanthoxylum piperitum* is in the range of 25 to 35% by weight of the composition, and wherein oral administration of the composition increases nutrient bioavailability in a subject.

2. The composition of claim 1, wherein the TRPV1 agonist further comprises *Capsicum annuum*.

3. The composition of claim 1, wherein the *Capsicum annuum* is in the range of 2 to 4% by weight of the composition.

4. The composition of claim 2, wherein the composition comprises the *Zingiber officinale* by weight in the range of 24 to 26%, the *Piper nigrum* by weight in the range of 3 to 5%, the *Capsicum annuum* by weight in the range of 2.5 to 3.5%, and the *Zanthoxylum piperitum* by weight in the range of 27 to 29%.

5. A method for increasing nutrient bioavailability in a subject in need thereof comprising orally administering to the subject an effective amount of the composition of claim 1.

6. The method of claim 5, wherein the composition further comprises *Capsicum annuum* in the range of 2 to 4% by weight of the composition.

7. The method of claim 6, wherein the *Zingiber officinale* is in the range of 24 to 26% by weight of the composition, the *Piper nigrum* is in the range of 3 to 5% by weight of the composition, the *Capsicum annuum* is in the range of 2.5 to 3.5% by weight of the composition, and the *Zanthoxylum piperitum* is in the range of 27 to 29% by weight of the composition.

\* \* \* \* \*